(12) United States Patent
Tung

(10) Patent No.: US 6,454,728 B1
(45) Date of Patent: Sep. 24, 2002

(54) APPARATUS AND METHOD FOR MONITORING NEUROMUSCULAR FUNCTION

(76) Inventor: Thomas J. K. Tung, 1212 Merediths Ford Rd., Baltimore, MD (US) 31286

( * ) Notice: Subject to any disclaimer, the term of this patent is extended or adjusted under 35 U.S.C. 154(b) by 6 days.

(21) Appl. No.: 09/796,892

(22) Filed: Mar. 2, 2001

(51) Int. Cl.$^7$ .......................... A61B 5/103; A61B 5/117
(52) U.S. Cl. ...................................... 600/587; 600/595
(58) Field of Search ................................ 600/546, 554, 600/587, 595

(56) References Cited

U.S. PATENT DOCUMENTS

| | | | | |
|---|---|---|---|---|
| 4,236,528 A | * | 12/1980 | Stanec et al. | 600/554 |
| 4,387,723 A | * | 6/1983 | Atlee, III et al. | 600/547 |
| 4,848,359 A | * | 7/1989 | Bournonville | 600/554 |
| 5,131,401 A | * | 7/1992 | Westenskow et al. | 600/554 |
| 5,885,231 A | * | 3/1999 | Cramer et al. | 600/595 |
| 6,165,148 A | * | 12/2000 | Carr-Stock | 602/21 |
| 6,315,736 B1 | * | 11/2001 | Tsutsumi et al. | 600/500 |

OTHER PUBLICATIONS

Walts, "The 'Bommerang'—A Method of Recording Adductor Pollicis Tension", *Canadian Anaesth. Soc. J.*, Sep. 1973, pp. 706–708, 20:5, California, USA.

"Paragraph" brochure, Utah Medical Products, Inc., Jul. 1992, USA.

Jenson et al., "The Accelograph®: a neuromuscular transmission monitor", *Acta Anaesthesiol Scand*, 1988, 32:49–52, Denmark.

Armstrong et al., "Measurement of neuromuscular blockade in man", *Anaesthesia*, 1977, 32:480–482.

Viby–Mogensen et al., "Measurement of acceleration: a new method of monitoring neuromuscular function", *Acta Anaesthesiol Scand*, 1988, 32:45–48, Denmark.

Baraka, "Monitoring of Neuromuscular Transmission in Anesthetized Man by a Bulb–Transducer Assembly", *Anesthesia and Analgesia . . . Current Researches*, Feb. 1973, 52:1, pp. 36–38, Lebanon.

"Biometer Accelograph" brochure, Richard's Medical Equipment, Inc.

Werner et al., "Assessment of neuromuscular transmission by the evoked acceleration response", *Acta Anaesthesiol Scand*, 1988, 32:395–400, Denmark.

May et al., "The acceleration transducer—an assessment of its precision in comparison with a force displacement transducer", *Acta Anaesthesiol Scand*, 1988, 32:239–243, Denmark.

Miller, Ed., "Tactile and Visual Evaluation of the Response to Train–of–four Nerve Stimulation", *Anesthesiology*, 1985, 63:440–443, USA.

Professional Instruments Price List, Jan. 1993.

"TOF–Watch® Objective and reliable monitoring of neuromuscular relaxation" brochure.

(List continued on next page.)

*Primary Examiner*—Kevin Shaver
*Assistant Examiner*—Charles Marmor, II
(74) *Attorney, Agent, or Firm*—Manelli Denison & Selter; Edward J. Stemberger

(57) ABSTRACT

An apparatus provided for monitoring thumb twitch includes a support structure constructed and arranged to support at least a hand of a patient. A pressurized biasing member is operatively associated with the support structure and located to contact the patient's thumb with the biasing member disposed between the thumb and support structure when the patient's hand is placed in the support structure. A pressure sensor is associated with the biasing member to generate an electrical signal corresponding to pressure exerted by the biasing member. A method of monitoring thumb twitch is also provided.

15 Claims, 2 Drawing Sheets

OTHER PUBLICATIONS

Lyew e al., "A simple device for monitoring neuromuscular blockade in children", *Can J Anaesth*, 1989, pp. 717–721, 36:6, Canada.

Viby–Mogensen, "Clinical Assessment of Neuromuscular Transmission", *Br J Anaesth*, 1982, 54:209–223.

Tyrrell, "The measurement of the force of thumb adduction", *Anaesthesia*, 1969, pp. 626–629, 24:4, USA.

Katz, "Comparison of Electrical and Mechanical Recording of Spontansous and Evoked Muscle Activity", *Anesthesiology*, Mar.–Apr. 1965, pp. 204–211, 26:2, USA.

* cited by examiner

APPARATUS AND METHOD FOR MONITORING NEUROMUSCULAR FUNCTION

BACKGROUND OF THE INVENTION

This invention relates to evaluating neuromuscular blockade by monitoring a thumb twitch response to train-of-four (TOF) nerve stimulation.

The use of muscle relaxants is an integral part of anesthetic management in present day practice. Currently, neuromuscular blockade is evaluated by determining the muscular reaction to train-of-four (TOF) nerve stimulation. There is equipment available for mechanical measurement of muscular response, such as the use of EMG, force displacement transducers, and most recently, the use of an acceleration transducer-based system of neuromuscular monitoring. These types of equipment, however, take time to set up and adjust, and are expensive. Because of these limitations, the daily routine use of such mechanical monitoring equipment is impractical. The evaluation of neuromuscular blockade therefore, at present, relies on the response, such as thumb twitch, to the TOF nerve stimulation which is evaluated either visually or manually (tactile).

Tactile or visual evaluation of neuromuscular blockade is subjective and involves uncertainty especially in the recovery phase. Furthermore, in certain surgical procedures when both hands are inaccessible, evaluation of the TOF by ulnar nerve stimulation is difficult or impossible. In such situations, muscle relaxants are given without clear objective criteria.

Accordingly, there is a need to provide a simple and inexpensive way of measuring the thumb twitch response to TOF stimulation during anesthesia.

SUMMARY OF THE INVENTION

An object of the present invention is to fulfill the need referred to above. This objective is obtained by providing a simple method for monitoring of the thumb twitch. The method uses an apparatus having a support structure configured for supporting at least a hand of a patient. The apparatus includes a pressurized biasing member operatively associated with the support structure and located to contact the patient's thumb when the patient's hand is placed in the support structure. A sensor is associated with the biasing member. The method includes placing the patient's hand in the support structure such that the thumb of the patient contacts the biasing member with the biasing member being disposed between the thumb and the support structure. The ulnar nerve is stimulated to cause the thumb to adduct and press the biasing member against the support structure with the sensor generating an electrical signal in response to the pressure exerted by the biasing member. The electrical signal is monitored.

In accordance with another aspect of the invention, an apparatus for monitoring thumb twitch includes a support structure constructed and arranged to support at least a hand of a patient. A pressurized biasing member is operatively associated with the support structure and located to contact the patient's thumb with the biasing member disposed between the thumb and support structure when the patient's hand is placed in the support structure. A pressure sensor is associated with the biasing member to generate an electrical signal corresponding to pressure exerted by the biasing member.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF THE INVENTION

Figure 1:
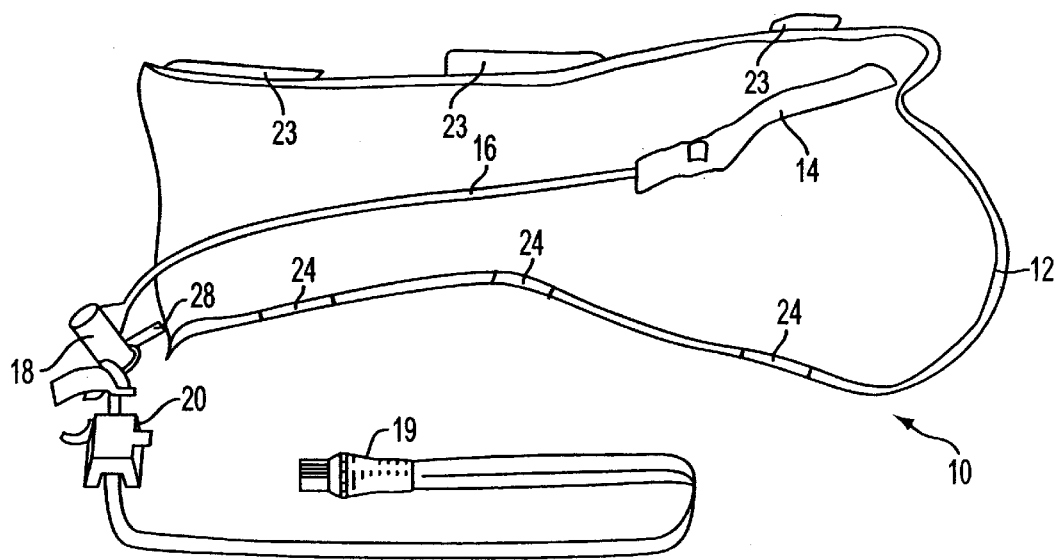
FIG. 1 is a view of a thumb twitch monitoring apparatus provided in accordance with the principles of the present invention.

Referring to FIG. 1, an apparatus for monitoring thumb twitch is shown, generally indicated 10, provided in accordance with the principles of the present invention. The apparatus 10 includes a rigid support structure 12 in the form of an anterior splinter type armboard constructed and arranged to receive a patient's hand and at least a portion of the forearm. The support structure 12, preferably molded form plastic, is configured to receive the wrist and fingers in a functional position.

Figure 2:
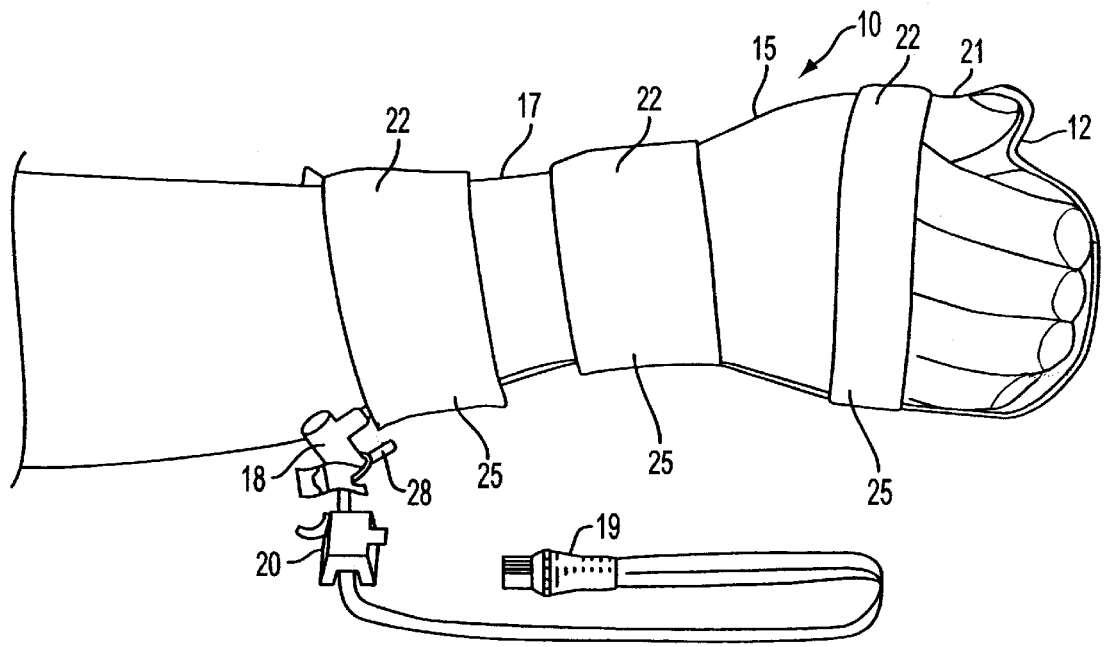
FIG. 2 is a view of a right forearm and hand placed in a support structure of the monitoring apparatus of FIG. 1.

The apparatus 10 includes a biasing member 14 operatively associated with the support structure 12. In the illustrated embodiment, the biasing member 14 is in the form of a elongated balloon, preferably sized 6×2 cm and having 8 ml capacity, fixed on the support structure 12 at a location corresponding to a thumb and thenar eminence location. The support structure 12 can be made to fit either the left or right forearm and hand. FIG. 2 shows the support structure receiving the right hand 15 and forearm 17 of a patient.

A connecting tubing structure 16 fluidly couples the balloon 14 through a conventional three-way stopcock connector 18 to a pressure transducer or sensor 20. The pressure sensor 20 can be any conventional physiological pressure transducer or sensor that can be used to measure arterial or venous pressure. In the illustrated embodiment, the pressure sensor 20 is a Transpac No. 46086-20 disposable transducer manufactured by Abbot Critical Care Systems.

In accordance with the invention, at least the patient's hand 15 is placed in the support structure 12 such that the thumb 21 of the patient contacts the biasing member 14, with the biasing member being disposed between the thumb and the support structure 12. In the embodiment of FIG. 2, the hand 15 and at least a portion of the forearm 17 of the patient is placed in the support structure 12 such that the hand 15 is further stabilized during the procedure. Fastening structure is provided to secure the hand 15 and the portion of the forearm 17 to the support structure 12. In the illustrated embodiment and as best shown in FIG. 2, the fastening structure comprises straps 22, each having one end 23 fixed to the support structure 12 at one side thereof. The support structure 12 has hook and loop fastening structure such as VELCRO® 24 coupled thereto, and the other, free end 25 of each strap 22 includes hook and loop fastening structure which mates with the hook and loop fastening structure 24 on the support structure 12. Thus, the straps 22 secure the forearm 17 and hand 15 of the patient to the support structure 12 and the arm can be placed in any position without restriction. It can be appreciated that other fastening structure such as buckles, buttons, etc can be employed instead of the hook and loop fastening shown.

Fluid, such as air or saline, is injected into stopcock connector 18 through port 28 so as to pressurize the biasing member 14 to a pressure of about 15–20 mm Hg. The ulnar nerve over the ulnar groove at the elbow is stimulated to elicit a strong thumb adduction (because of stimulation of the flexor carpi ulnaris muscle), causing the thumb to press the biasing member 14 against the support structure 12. The pressure exerted by the biasing member 14 is transmitted to the pressure sensor 20 with the pressure sensor 20 generating an electrical signal in response to the exerted pressure. The pressure sensor 20 includes a connector 19 which is constructed and arranged to be connected to a conventional vital signs monitoring device (not shown) to display the electrical signal.

As shown in FIGS. 3A–3H, an electrocardiogram and blood pressure of the patient can be monitored simultaneously with the monitoring of the signal generated by the pressure sensor 20.

Figure 3D:
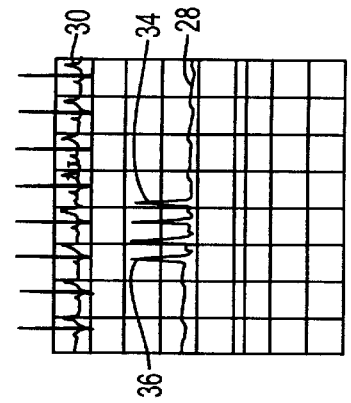
FIGS. 3A to 3H show typical recording of a thumb twitch response to TOF stimulation as measured by the apparatus of FIG. 1, before, during and following reversal of pancuronium neuromuscular blockade in a patient under nitrous oxide-narcotic anesthesia.
Figure 3H:
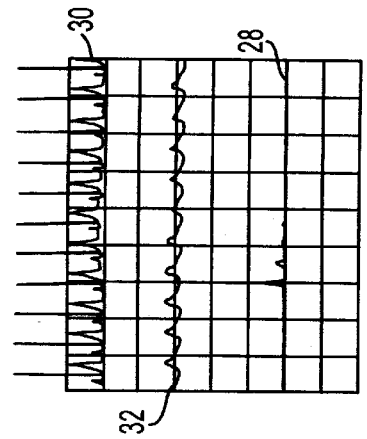
Figure 3C:
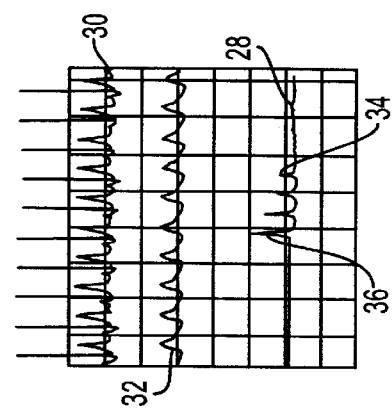
Figure 3G:
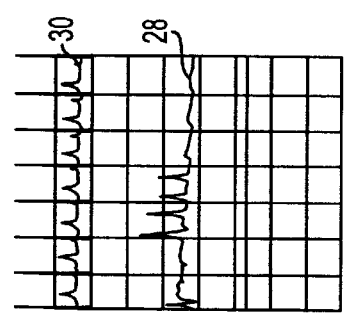
Figure 3B:
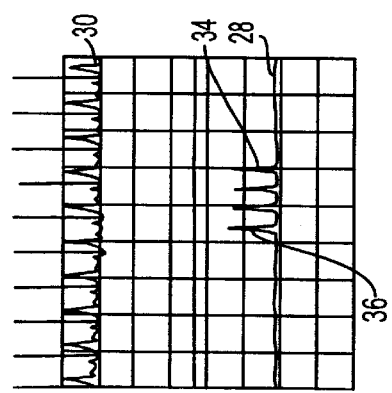
Figure 3F:
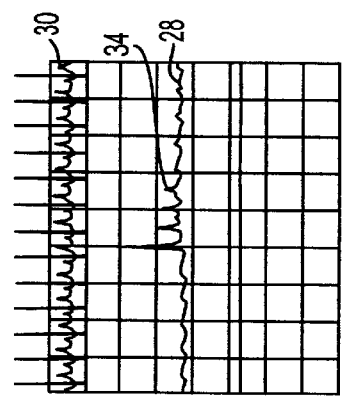
Figure 3A:
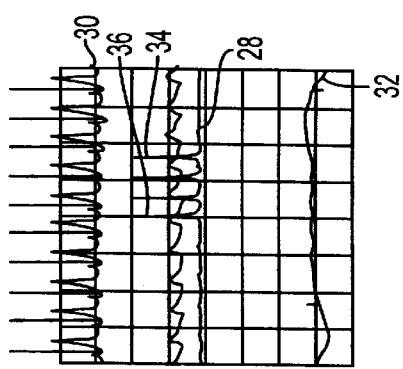
Figure 3E:
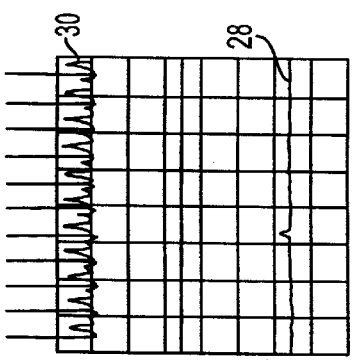

FIGS. 3A–3H show typical signal recordings 28 (of the electrical signal from pressure sensor 20) corresponding to thumb twitch responses to train-of-four (TOF) stimulation before, during and following reversal of pancuronium neuromuscular blockade in a patient under nitrous oxide-narcotic anesthesia. As shown, an ECG signal 30 and/or arterial blood pressure signal 32 can also be recorded. FIGS. 3A–3B show recordings before the blockade. Note the height of fourth twitch 34 is equal to the height of the first twitch 36. The T4 ratio (the ratio of the height of the fourth to the first twitch) is 100%. FIGS. 3C–3E show recordings during the blockade. Note there is a gradual decrease in height of the fourth twitch 34 in relation to the first twitch 36 and eventually only the response to the first of the four stimulations of TOF remain. FIGS. 3F–3G show recordings during the recovery phase of the blockade. Note the gradual return of the fourth twitch 34. FIG. 3H shows recordings following the reversal of the blockade, the height of the fourth twitch 34 has became equal to the height of the first twitch 36. T4 ratio is now again 100%.

The advantages of the apparatus and method are:
1. The apparatus is simple and easy to apply.
2. The apparatus is inexpensive and can be reused.
3. The apparatus utilizes an existing pressure channel of the monitor.
4. Once secured, the hand with the apparatus can be placed away from the anesthesiologist.
5. Remote monitoring is possible when both upper extremities are hidden under the surgical drapes and are inaccessible to the anesthesiologist.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of monitoring thumb twitch using an apparatus having a support structure configured for supporting at least a hand of a patient, the apparatus including a pressurized biasing member operatively associated with the support structure and located to contact the patient's thumb when the patient's hand is placed in the support structure, and a sensor associated with the biasing member, the method including the steps of:

placing the patient's hand in the support structure such that the thumb of the patient contacts the biasing member with the biasing member being disposed between the thumb and the support structure, stimulating the ulnar nerve to cause the thumb to adduct and press the biasing member against the support structure with the sensor generating an electrical signal in response to the pressure exerted by the biasing member, and monitoring the electrical signal, wherein the biasing member is a balloon and the method includes injecting air into the balloon to a pressure of 15–20 mm Hg prior to the stimulating step.

2. The method of claim 1, further including monitoring an electrocardiogram of the patient as the electrical signal is monitored.

3. The method of claim 1, further including monitoring blood pressure of the patient as the electrical signal is monitored.

4. The method of claim 1, wherein the support structure is constructed and arranged to support a hand and forearm of the patient, the method including placing and securing the hand and forearm in the support structure.

5. An apparatus for monitoring thumb twitch, the apparatus comprising a support structure constructed and arranged to support at least a hand of a patient, a pressurized biasing member operatively associated with the support structure and located to contact the patient's thumb with the biasing member disposed between the thumb and support structure when the patient's hand is placed in the support structure, and a pressure sensor associated with the biasing member to generate an electrical signal corresponding to pressure exerted by the biasing member, wherein the biasing member is a balloon pressurized with fluid.

6. The apparatus of claim 5, wherein the biasing member is fixed to the support structure.

7. The apparatus of claim 5, wherein the fluid is air.

8. The apparatus of claim 5, wherein the support structure is made of rigid material.

9. The apparatus of claim 5, wherein the support structure is constructed and arranged to conform to and receive the hand and at least a portion of the forearm of the patient.

10. The apparatus of claim 9, further comprising fastening structure to secure the hand and portion of the forearm to the support structure.

11. The apparatus of claim 10, wherein the fastening structure includes at least one strap having one end fixed to the support structure, the support structure having hook and loop fastening structure coupled thereto, and the other end of the strap including hook and loop fastening structure which mates with the hook and loop fastening structure on the support structure such that the other end of the strap can be removably coupled to the support structure.

12. The apparatus of claim 11, wherein three straps are provided.

13. The apparatus of claim 5, wherein the pressure sensor includes a connector constructed and arranged to connect with a monitoring device.

14. An apparatus for monitoring thumb twitch, the apparatus comprising
 a support structure constructed and arranged to support at least a hand of a patient,
 a pressurized biasing member operatively associated with the support structure and located to contact the patient's thumb with the biasing member disposed between the thumb and support structure when the patient's hand is placed in the support structure, and
 a pressure sensor associated with the biasing member to generate an electrical signal corresponding to pressure exerted by the biasing member,
 wherein a tube structure fluidly couples the biasing member to the pressure sensor.

15. The apparatus of claim 14, wherein a three-way stopcock is provided in the tube structure for supplying the biasing member with fluid.

* * * * *